(12) United States Patent
Odidi et al.

(10) Patent No.: US 7,858,119 B1
(45) Date of Patent: *Dec. 28, 2010

(54) EXTENDED RELEASE PHARMACEUTICALS

(76) Inventors: Amina Odidi, 200 Walmer Road, Toronto, Ontario (CA) M5R 3R7; Isa Odidi, 200 Walmer Road, Toronto, Ontario (CA) M5R 3R7

(*) Notice: Subject to any disclaimer, the term of this patent is extended or adjusted under 35 U.S.C. 154(b) by 0 days.

This patent is subject to a terminal disclaimer.

(21) Appl. No.: 09/845,497

(22) Filed: May 1, 2001

Related U.S. Application Data

(60) Provisional application No. 60/203,049, filed on May 9, 2000.

(51) Int. Cl.
*A61K 9/48* (2006.01)
*A61K 9/22* (2006.01)
*A61K 9/28* (2006.01)
*A61K 9/50* (2006.01)

(52) U.S. Cl. .................. 424/463; 424/468; 424/474; 424/490

(58) Field of Classification Search .................. 424/452, 424/463, 468, 474, 490
See application file for complete search history.

(56) References Cited

U.S. PATENT DOCUMENTS

| | | | | |
|---|---|---|---|---|
| 5,800,422 A | * | 9/1998 | Dong et al. | 604/892.1 |
| 5,955,106 A | | 9/1999 | Moeckel et al. | |
| 6,039,975 A | * | 3/2000 | Shah et al. | 424/473 |
| 6,099,859 A | * | 8/2000 | Cheng et al. | 424/464 |
| 6,106,864 A | * | 8/2000 | Dolan et al. | 424/488 |
| 6,312,724 B1 | * | 11/2001 | Odidi et al. | 424/468 |
| 6,509,037 B2 | * | 1/2003 | Odidi et al. | 424/468 |
| 6,652,882 B1 | * | 11/2003 | Odidi et al. | 424/486 |
| 6,676,966 B1 | * | 1/2004 | Odidi et al. | 424/464 |

FOREIGN PATENT DOCUMENTS

JP 03197421 * 8/1991

OTHER PUBLICATIONS

Google search for the definition of ethyl cellulose completed Sep. 27, 2007.*

* cited by examiner

*Primary Examiner*—Alton N Pryor

(57) ABSTRACT

An extended release pharmaceutical formulation is disclosed. A selected pharmaceutical agent is encased within polymeric film layers providing for gradual release of the pharmaceutical active for over 12 and even 24 hours in the gastrointestinal tract and the blood plasma.

22 Claims, No Drawings

EXTENDED RELEASE PHARMACEUTICALS

RELATED APPLICATIONS

This application claims priority to U.S. Provisional Application Ser. No. 60/203,049, filed May 9, 2000.

FIELD OF THE INVENTION

The present invention relates to pharmaceutical formulation compositions and method of producing extended release dosage forms of pharmaceutical agent(s).

BACKGROUND OF THE INVENTION

It is known that food may decrease the extent and or delay of the absorption of pharmaceutical agents, as shown by lower peak concentration and lower AUC in plasma and a prolongation of time to peak plasma concentration following administration of a single immediate release tablet a pharmaceutical agent with food, compared to the same tablet strength administered without food. Very often these pharmaceutical agents are marketed as immediate release formulation and have to be administered several times a day a situation that has raised concerns regarding patient compliance. There are also pharmaceutical agents that can't be taken with food because food may decreases their bioavailability.

Limited research work has been done to address these problems and no successful work has been reported on an extended release pharmaceutical composition or dosage form-that when taken with meals does not result in a decrease in bioavailability.

Current drug delivery techniques such as matrix tablets, osmotic tablets and delayed release tablets are not suitable because the extent of drug release or bioavailability is not optimal or does not provide sufficient coverage over a 12 hours and 24 hours period when taken with food. Furthermore, for coated tablets the choice of coating polymer(s) makes large scale or commercial production of consistent and reproducible batches difficult if not impossible. The manufacturing process for these formulations involves long process times and large number of process steps, requiring qualification, cleaning and validation. Stability problems during manufacture and storage may be an issue with current controlled systems especially for the delivery of large doses.

SUMMARY OF THE INVENTION

The present invention relates mainly to a formulation composition and method of producing extended release formulations containing pharmaceutical agent(s); more specifically, the present invention relates to an oral dosage formulation comprising a pharmaceutical agent(s) that have to be taken with food in order for them to be better tolerated as gastrointestinal symptoms usually associated with their use may be minimized.

It is an object of the present invention to provide an extended and controlled release composition and formulation of pharmaceuticals that can provide detectable blood levels of the said agent over 12 hours and or over 24 hours when given to humans or animals thus allowing for twice and/or once daily administration.

It is also an object of the present invention to provide an extended and controlled release composition and formulation of pharmaceuticals that does not employ a matrix-type tablet or contain an expandable, gelling, swellable hydrocolloid polymer as a retardant agent.

It is a further object of the present invention to provide an extended and controlled release composition and formulation of pharmaceuticals that does not employ sustained-release microcapsules.

It is a further object of the present invention to provide an extended and controlled release composition and formulation of pharmaceuticals that does not employ a gas driven dispensing device and gas generating engine to dispense a beneficial agent.

It is also a further object of the present invention to provide an extended and controlled release composition and formulation of pharmaceuticals that is not a granular sustained-release formulation of effervescent water-dispersible tablet.

It is a further object of the present invention to provide an extended and controlled release composition and formulation of pharmaceuticals that is not a controlled release pharmaceutical tablet comprising a core containing the pharmaceuticals, a semipermeable coating membrane surrounding the core with passageway(s) in the membrane.

It is also an object of the present invention to provide an extended and controlled release composition and formulation of pharmaceuticals in which the rate of input and the extent of release (bioavailability) of the agent is reduced compared to an immediate release formulation of same dosage strength when administered under fasting condition but increased or remain unchanged when given with food.

It is also an object of the present invention to provide an extended and controlled release composition and formulation of pharmaceuticals in which there is a lag phase before the gradual release of the agent is begun in which the timing, rate and extent of drug release is pH dependent.

According to an aspect of the present invention, there is provided an extended release pharmaceutical active formulation comprising: pharmaceutical active; and an encasement coat in the faun of one or more layers of pH sensitive polymeric film encasing said pharmaceutical active; wherein said polymeric film is soluble in a pH of about above 5.0.

In accordance with another aspect of the present invention there is an extended release pharmaceutical active formulation comprising: a capsule, tablet, pellet or bead of pharmaceutical active; an encasement coat in the form of one or more layers of a pH sensitive polymeric film encasing said capsule, tablet, pellet or bead; wherein said polymeric film is soluble above a pH of about 5.0.

In accordance with yet another aspect of the present invention there is an extended release pharmaceutical active formulation comprising: a capsule, tablet, pellet or bead of pharmaceutical active comprising about 5-95% by weight pharmaceutical active; about 0-60% by weight pharmaceutical compression aid; and about 0-50% by weight pharmaceutical extrusion aid; and an encasement coat in the form of one or more layers of a pH sensitive polymeric film encasing said capsule, tablet, pellet or bead, said encasement coat comprising about 5-55% by weight polymer; and about 0.5-30% by weight plasticizer; wherein said polymeric film is soluble above a pH of about 5.0.

In accordance with yet another aspect of the present invention there is a method for making an extended release pharmaceutical active formulation comprising: compressing pharmaceutical active into tablets, pellets or beads; encasing said tablets, pellets or beads in an encasement coat in the form of one or more layers of a pH sensitive polymeric film, said encasement coat comprising about 5-55% by weight polymer; and about 0.5-30% by weight plasticizer; wherein said polymeric film is soluble above a pH of about 5.0.

DETAILED DESCRIPTION OF THE INVENTION

Through intensive investigation to resolve the above problems and achieve the foregoing objectives, the present inventors found it surprisingly possible to produce extended and controlled release composition and formulation containing pharmaceutical actives presented in form of: a non gas driven, non hydrogelling, non swelling or non matrix tablet made by dry granulation or direct compression of the pharmaceuticals; the pharmaceutical active tablet is encased in one or more layers of pH solubility dependant polymeric film(s) which is not semipermeable, non permeable, non swellable and has no passage way; which is insoluble in acid media and dissolve by salt formation above pH 5-6.

Surprisingly, the present invention when ingested in the presence of food is capable of providing more than 12 hours and or more than 24 hours of delivery of the pharmaceuticals in the gastrointestinal tract and blood plasma without a decrease in the extent of release or bioavailability.

The present invention is an extended release pharmaceutical active formulation that comprises pharmaceutical active that can be in the form of a capsule, tablet, pellet or bead which is encased with an encasement coat in the form of one or more layers of a pH sensitive polymeric film that is soluble above a pH of about 5.0. The capsule, tablet, pellet or bead of pharmaceutical active comprises about 5-95% by weight pharmaceutical active, optionally about 0-60% by weight pharmaceutical compression aid, and optionally about 0-50% by weight of a pharmaceutical extrusion aid. The pharmaceutical compression aid may be selected from the group consisting of lactose, cellulose, dibasic calcium phosphate dihydrate, calcium sulfite dihydrate, tricalcium phosphate and compressible sugar. The capsule, tablet, pellet or bead of pharmaceutical active may optionally comprise excipients, lubricants, binders or glidants.

The encasement coat comprises about 5-55% by weight polymer and about 0.5-30% by weight plasticizer. The encasement coat may be a polymeric film which is a polymer selected from the group consisting of cellulose esters, polyvinyl acetate phthalate, methacrylic acid copolymer type A, methacrylic acid copolymer type B, methacrylic acid copolymer type C and any mixtures thereof. The encasement coat may be a polymeric film composed of shellac or zein.

The present invention further provides a method for making pharmaceutical active tablets preferably by dry granulation or direct compression and encasement of the tablet in at least one layer of pH sensitive polymeric film(s). Dry granulation can be accomplished by slugging. The tablet may also be made by first processing pharmaceuticals alone or with suitable excipients via wet granulation or fluid bed granulation or spray drying before tabletting. To the tablet is optionally added 0-60% by weight of one or more pharmaceutical compression aids such as lactose, cellulose, dibasic calcium phosphate dihydrate, calcium sulfite dihydrate, tricalcium phosphate, and compressible sugar which have high compactibility, good flowability and blending properties and good stability. To the tablet is also optionally added 0-50% by weight extrusion aids. The tablet may also contain lubricants, binders or glidants.

The polymeric film(s) are applied to the pharmaceutical active being composed of 0.5 to 30% of cellulose esters or polyvinyl acetate phthalate or methacrylic acid copolymer type A or methacrylic acid copolymer type B or methacrylic acid copolymer type C or any mixture thereof. The polymeric film displays pH sensitive solubility such that it is insoluble in acid medium but soluble in alkaline medium. The polymeric film(s) may be replaced by shellac or Zein. The polymeric film(s) may contain plasticizers, antitacking agents, colorants and antihyperglycemic agent(s).

Examples of pharmaceutical actives that will benefit from the present invention include but are not limited to risedronate, alendronate, riluzole, sulfonylureas including glyburide, chlorpropamide, tolbutamide, glimepiride, acarbose (Precose)™, alglucerase (Ceredase)™, glimepiride (Amaryl)™, miglitol (Glyset)™, nateglinide (Starlix)™, pimagidine, pioglitazone, (Actos)™, pramlintide, repaglinide (Prandin)™, rosiglitazone (Avandia)™, troglitazone (Rezulin)™, hypoglycemic benzenesulfonamido pyrimidines, buformin, phenformin and 1,2-Biguanides.

Further pharmaceutical agents that can be delivered within the extended release formulation are with this invention are bioactive peptides, antitumor agents, antibiotics, antipyretic analgesic antiinflammatory agents, antitussive expectorants, sedatives, muscle relaxants, antiepileptics, antiulcer agents, antidepressants, anti-allergic agents, cardiotonics, antiarrhythmic agents, vasodilators, hypotensive diuretics, anticoagulants, hemolytics, antituberculosis agents, hormones, narcotic antagonists, bone resorption suppressors and angiogenesis suppressors. One skilled in the art would readily be able to select a desired pharmaceutical agent for incorporation into the present formulation.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Methods of chemistry, biochemistry and pharmacology referred to but not explicitly described in this disclosure and examples are reported in the scientific literature and are well known to those skilled in the art.

Example 1

An extended release tablet of acarose 75 mg, 150 mg and 300 mg is prepared according to the present invention as follows:

1(a) Manufacture of the Non-Encased Tablets or Pellets

|  | Formulation A | Formulation B |
| --- | --- | --- |
| Acarbose | 55.0% | 65.5% |
| Silicon dioxide | 0.5% | — |
| Dibasic Calcium phosphate dihydrate | 44.5% | — |
| Microcrystalline cellulose | — | 34.0% |
| Magnesium stearate | 1.0% | 0.5% |

The acarbose and silicon dioxide were mixed in a high shear mixer. The mixture was discharged into a v-blender to which was added microcrystalline cellulose and magnesium stearate. The mixture in the v-blender was blended until a homogeneous blend was obtained. The mixture in the v-blender was discharged after blending and compressed into tablets or pellets or beads. The pellets or beads can be manufactured by extrusion spheronization in which a wet mass of the composition is extruded alone or with aid of extruding aids and spheronized.

1(b) Dissolution Testing of Non-Encased Tablets or Pellets or Beads

The non-encased tablets or pellets or beads were tested in degassed water.

| Dissolution medium: Degassed water | |
|---|---|
| Time | Amount dissolved |
| 1 hr | >80% |

1(c) Manufacture of Encasement Dispersion

| | Formulation 1 | Formulation 2 | Formulation 3 |
|---|---|---|---|
| Methacrylic acid copolymer type A | 15.5% | 15.0% | — |
| Methacrylic acid copolymer type B | — | 5.0% | 15.0% |
| Polyethylene glycol 600 | 1.0% | 1.5% | 1.5% |
| Talc | 3.5% | 3.0% | 3.0% |
| Water and/or Ethanol quantity sufficient | 100.0% | 100.0% | 100.0% |

Add Polyethylene glycol was added to the aqueous dispersion of methacrylic acid copolymer(s) and mixed. Talc was added while stirring with a propeller mixer. Polyethylene glycol is used as a plasticizer to help enhance the elasticity of the film(s)

1(d) Application of the Encasement Film(S) and Manufacture of Encased Tablets or Pellets The non-encased tablets or pellets or beads were charged into a perforated coating pan in a pan coater. The inlet air temperature was adjusted so as to have tablet bed temperature at 30° C. Pan speed was set at between 6 and 10 rpm. The spray rate for applying the film(s) on a continuous basis was 3 g per minute per kg tablets. The atomization pressure was from 1.5 to about 4 bar. A coating level of about 0.5 to 15 mg of polymer per square centimeter of tablet surface area and preferably 3 to 7 mg/cm2 was applied. Beads may also be coated using a fluid bed dryer.

1(e) Dissolution Testing of Encased Tablets

The present invention which consist (encased tablets) were tested in Gastric fluid, simulated TS, and Intestinal fluid, simulated TS in accordance to USP 23_NF 18.

| Dissolution medium: Gastric fluid, simulated | | Dissolution medium: Intestinal fluid, simulated | |
|---|---|---|---|
| Time | Amount dissolved | Time | Amount dissolved |
| 1 hr | <10% | 1 hr | >80% |

The invention claimed is:

1. An extended release pharmaceutical active formulation comprising:

a capsule, tablet, pellet, or bead comprising about 5-95% by weight pharmaceutical active and an aid selected from the group consisting of a pharmaceutical compression aid and a pharmaceutical extrusion aid and mixtures thereof, wherein said compression aid is selected from the group consisting of lactose, cellulose, dibasic calcium phosphate dihydrate, calcium sulfite dihydrate, tricalcium phosphate and compressible sugar;

an encasement coat comprising one or more layers of a polymeric film encasing said capsule, tablet or pellet, said encasement coat being non-permeable, having no passage way and being soluble in a pH of above 5.0 and comprising about 5 up to 55% by weight polymer and about 0.5%-30% by weight plasticizer of polyethylene glycol, wherein said formulation provides over 12 hours of extended release of said active in the blood plasma.

2. The formulation of claim 1, wherein said compression aid is present in an amount of up to about 60% by weight.

3. The formulation of claim 1, wherein said extrusion aid is present in an amount of up to about 50% by weight.

4. The formulation of claim 1, wherein said formulation additionally comprises excipients, lubricants, binders or glidants.

5. The formulation of claim 1, wherein said polymeric film is a polymer selected from the group consisting of cellulose esters, polyvinyl acetate phthalate, methacrylic acid copolymers type A, methacrylic acid copolymer type B, methacrylic acid copolymer type C and any mixtures thereof.

6. The formulation of claim 1, wherein said polymeric film comprises shellac or zein.

7. The formulation of claim 1, wherein said pharmaceutical active is selected from the group consisting of risedronate, alendronate, riluzole, and sulfonylureas.

8. The formulation of claim 1, wherein said pharmaceutical active is selected from the group consisting of bioactive peptides, antitumor agents, antibiotics, antipyretic analgesic anti-inflammatory agents, antitussive expectorants, sedatives, muscle relaxants, antiepileptics, antiulcer agents, antidepressants, anti-allergic agents, cardiotonics, antiarrhythmic agents, vasodilators, hypotensive diuretics, anticoagulants, hemolytics, antituberculosis agents, hormones, narcotic antagonists, bone resorption suppressors and angiogenesis suppressors.

9. The formulation of claim 7, wherein said polymeric film further comprises an agent selected from the group consisting of plasticizers, antitacking agents, colorants and mixtures thereof.

10. The formulation of claim 1, wherein greater than 80% of said pharmaceutical active is released in one hour when tested in a USP apparatus at 100 rpm in 900 ml degassed water and at 37° C.

11. The formulation of claim 1, wherein less than about 20% of the pharmaceutical active is released in one hour when tested in a USP apparatus at 75 rpm in 900 ml simulated gastric fluid (pH 1.2 phosphate buffer) and at 37° C. and greater than 80% of the pharmaceutical active is released in one hour when tested in a USP apparatus at 75 rpm in 900 ml simulated intestinal fluid (pH 7.5 phosphate buffer) and at 37° C.

12. The formulation of claim 1, wherein the tablet or pellet is made by direct compression.

13. The formulation of claim 7, wherein the release of the pharmaceutical active exhibits a lag phase (time) and after which release is extended over 12 hours or 24 hours after administration.

14. The formulation of claim 1, wherein the capsule, tablet, pellet or bead demonstrates extended release characteristics of greater than 24 hours when tested in a USP apparatus at 100 rpm in 900 ml degassed water and at 37° C.

15. The formulation of claim 1, wherein said capsule, tablet, pellet or bead demonstrates extended release characteristics of greater than 24 hours when tested in a USP apparatus at 75 rpm in 900 mls simulated gastric fluid (pH 1.2 phosphate buffer) and at 37° C. and demonstrates extended release characteristics of greater than 24 hours when tested in a USP apparatus at 75 rpm in 900 mls simulated intestinal fluid (pH 7.5 phosphate buffer) and at 37° C.

16. The formulation of claim 1, wherein said pharmaceutical active is selected from the group consisting of glyburide, chlorpropamide, tolbutamide, glimepiride, acarbose, alglucerase, miglitol, nateglinide, pimagidine, pioglitazone, pramlintide, repaglinide, rosiglitazone, troglitazone, hypoglycemic benzenesulfonamido pyrimidines, buformin and phenformin.

17. An extended release pharmaceutical active formulation comprising:
   a capsule, tablet, pellet or bead of about 5-95% by weight pharmaceutical active, about 0-60% by weight pharmaceutical compression aid selected from the group consisting of lactose, cellulose, dibasic calcium phosphate dihydrate, calcium sulfite dihydrate, tricalcium phosphate and compressible sugar, and about 0-50% by weight pharmaceutical extrusion aid,
   an encasement coat comprising one or more layers of a polymeric film encasing said capsule, tablet, pellet or bead, said encasement coat being non-permeable, having no passage way and being soluble in a pH of above about 5.0 and comprising about 5 up to less than 50% by weight polymer and about 0.5%-30% by weight polyethylene glycol,
   wherein said formulation provides over 12 hours of extended release of said active in the blood plasma.

18. The formulation of claim 17, wherein said polymeric film is a polymer selected from the group consisting of cellulose esters, polyvinyl acetate phthalate, methacrylic acid copolymers type A, methacrylic acid copolymer type B, methacrylic acid copolymer type C and any mixtures thereof.

19. The formulation of claim 18, wherein pharmaceutical active release exhibits a lag phase (time) after which release is extended over 12 hours or 24 hours when administered to humans or animals in the presence of food.

20. An extended release pharmaceutical active formulation comprising:
   a capsule, tablet, pellet or bead of pharmaceutical active comprising;
      about 5-95% by weight pharmaceutical active;
      about 0-60% by weight pharmaceutical compression aid;
      about 0-50% by weight pharmaceutical extrusion aid; and
   an encasement coat comprising one or more layers of a polymeric film encasing said capsule, tablet, pellet or bead of said pharmaceutical active, said encasement coat being non-permeable, having no passage way and being soluble in a pH of above about 5.0 and comprising about 5 up to 55% by weight polymer and about 0.5%-30% by weight plasticizer comprising polyethylene glycol,
   wherein said formulation provides over 12 hours of extended release of said active in the blood plasma.

21. A method for making an extended release pharmaceutical active formulation comprising:
   compressing about 5-95% by weight pharmaceutical active into a capsule, tablet, pellet or bead with an aid selected from the group consisting of a pharmaceutical compression aid and a pharmaceutical extrusion aid and mixtures thereof, wherein said compression aid is selected from the group consisting of lactose, cellulose, dibasic calcium phosphate dihydrate, calcium sulfite dihydrate, tricalcium phosphate and compressible sugar;
   encasing said capsules, tablets, pellets, or beads in an encasement coat comprising one or more layers of a polymeric film, said encasement coat being non-permeable, having no passage way and being soluble in a pH of above 5.0 and comprising about 5 up to 55% by weight polymer and about 0.5%-30% by weight plasticizer of polyethylene glycol,
   wherein said formulation provides over 12 hours of extended release of said active in the blood plasma.

22. The method of claim 21, wherein said pharmaceutical compression aid is present in an amount of up to about 60% by weight and said pharmaceutical extrusion aid is present in an amount of up to about 50% by weight.

* * * * *